United States Patent [19]

Dougherty et al.

[11] Patent Number: 4,814,493

[45] Date of Patent: Mar. 21, 1989

[54] PROCESS FOR PRODUCTION OF ALKYL ACRYLATES

[75] Inventors: Edward F. Dougherty, Galveston; Mark O. Scates; James L. Paul, both of Harris, all of Tex.

[73] Assignee: Hoechst Celanese Corporation, Somerville, N.J.

[21] Appl. No.: 510,845

[22] Filed: Jul. 5, 1983

[51] Int. Cl.$^4$ .............................................. C07C 69/52
[52] U.S. Cl. .................................... 560/205; 560/217; 560/235
[58] Field of Search ........................ 560/205, 217, 235

[56] References Cited

U.S. PATENT DOCUMENTS

| | | | |
|---|---|---|---|
| 2,916,512 | 12/1959 | Fisher et al. | 560/205 |
| 3,238,239 | 3/1966 | Schweckendick et al. | 560/205 |
| 3,392,191 | 7/1968 | Ensor et al. | 560/205 |
| 3,686,268 | 8/1972 | Jobert et al. | 560/217 |
| 4,161,609 | 7/1979 | Cramer | 560/205 |
| 4,355,136 | 10/1982 | Dumbroski et al. | 525/35 |

OTHER PUBLICATIONS

Schultheis, Heing et al., *Chemical Abstracts*, vol. 54 (1960), #21,852f.

Otani, Nobuta, *Chemical Abstracts*, vol. 66 (1964), #8151h-8152a.

Kirk-Othmer, *Encyclopedia of Chemical Technology*, 2nd Ed., vol. 1, p. 299.

*Primary Examiner*—Paul J. Killos
*Attorney, Agent, or Firm*—Marvin Turken; Linn I. Grim

[57] ABSTRACT

This invention describes an improved process for the production of $C_1$–$C_8$ alkyl acrylate by the reaction of a $C_1$–$C_8$ alkyl alcohol with acrylic acid in the presence of esterification catalysts and soluble manganese or cerium ions.

11 Claims, 1 Drawing Sheet

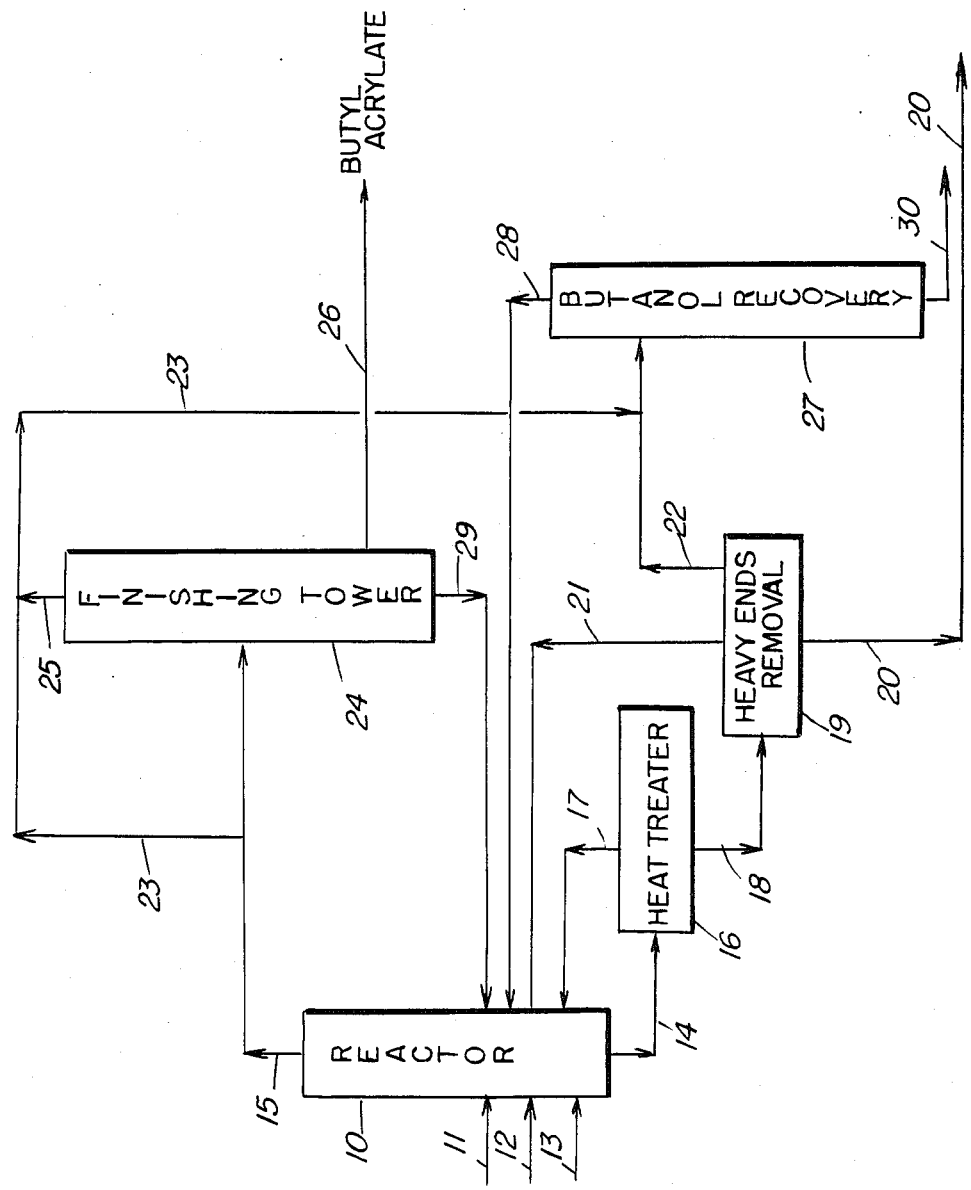

PROCESS FOR PRODUCTION OF ALKYL ACRYLATES

This invention relates to an improved process for producing an alkyl acrylate by the reaction of an alkyl alcohol with acrylic acid containing a phenolic type inhibitor in the presence of soluble manganese or cerium metal ions.

BACKGROUND OF THE INVENTION

Processes for the production of an alkyl acrylate by the reaction of an alkyl alcohol with acrylic acid in the presence of an esterification catalysts are well known. To provide improvements in these processes without the use of new esterification catalysts, are unusual and unique.

In the known esterification processes, the acrylic acid used normally contains inhibitors which prevent undesired polymerization prior to use. The inhibitors commonly used are phenothiazine, methylene blue, phenolic type inhibitors such as hydroquinone, p-methoxyphenols and the like. It is not generally known to use a metal additive in combination with organic inhibitors in acrylic acid. In Chemical Abstracts Vol. 74,1971, 112642V, a Japanese patent (70-35,285) filed June 1, 1967, assigned to Nippon Kayaku, Co. Ltd., describes the mixture of chromium acetate with hydroquinone as a satisfactory inhibitor for acrylic acid and methacrylic acid. In Japanese Patent Publication No. 51-98211, filed Feb. 15, 1975 assigned to Sumitomo Chemical Co. Ltd., the combination of a manganese salt and phenolic type inhibitors provided satisfactory stabilization of acrylic acid. In copending application entitled "Stabilized Ethylenically Unsaturated Organic Compounds" Ser. No. 510,870, filed July 5, 1983 and assigned to the same assignee as the present application, describes the use of cerium in combination with other inhibitors as an inhibitor for polymerizable ethylenically unsaturated organic compounds. In copending application entitled "Improved Process for Production of Ethyl Acrylate" Ser. No. 06/510,846 filed July 5, 1983 assigned to the same assignee as the present application, there is described an improved process in the production of ethyl acrylate by the reaction of ethylene and acrylic acid containing polymerization inhibitors especially phenolic type polymerization inhibitors in the presence of sulfuric acid and in the presence of manganese or cerium metal ions soluble in the reaction mixture. Improved efficiencies of ethyl acrylate production from acrylic acid are achieved using this procedure. In this invention, improvements have been achieved in an esterification reaction of an alkyl alcohol and acrylic acid containing phenolic type inhibitors to produce an alkyl acrylate in the presence of manganese or cerium metal ions soluble in the reaction mixture.

THE INVENTION

In the reaction mixture of acrylic acid containing phenolic type inhibitors, an alkyl alcohol containing 1 to 8 carbon atoms and an esterification catalyst, it has been discovered that if metal ions of manganese or cerium, soluble in the reaction mixture, are present, improvements in efficiencies and yields of an alkyl acrylate containing 1 to 8 carbon atoms from acrylic acid, are achieved. It has also been observed that unexpectedly corrosion rates of the stainless steel reactors are reduced in the use of the soluble manganese or cerium metal ions in the process of this invention compared to the corrosion rates with the metal ions not being present.

The accompanying drawing is a simplified schematic flow sheet exemplifying the preparation of an alkyl acrylate from an alkyl alcohol and acrylic acid using the process of this invention.

To achieve the improvements of this invention, a batch or continuous process can be used. The process schematically represented in the drawing is a continuous process and especially useful in the production of butyl acrylate from butanol and acrylic acid. This process includes a combination of butanol supplied through line 11, esterification catalyst such as methanesulfonic acid supplied through line 12 and acrylic acid containing a phenolic type inhibitor supplied through line 13 into reactor 10. Manganese or cerium metal ions can be supplied to the reactor by combining these metal ions with either butanol, the esterification catalyst and acrylic acid or added separately, however, the best results were achieved when Mn or Ce is added during acrylic acid processing prior to being used as feed to the esterification reactors, if desired. The reactor is stirred while maintaining reaction temperatures in the range from about 100° C. to about 150° C., preferably from about 110° C. to about 120° C. under reduced pressures from about 100 mm Hg to about 300 mm Hg, preferably from about 150 mm Hg to about 270 mm Hg. The amount of esterification catalyst maintained in the reactor ranges from about 1 to about 5 weight percent of the total reactants, preferably from about 2 to about 4 weight percent of the total reactants.

The butyl acrylate reaction product is removed from the reactor through line 15 and sent to the finishing distillation tower 24 maintained at temperatures from about 85° C. to about 93° C. The bottom reactor residue containing polymer, butyl acrylate, butanol and water are removed from reactor 10 through the line 14 and sent to a heat treater 16 maintained at temperatures from about 200° C. to about 240° C. to recover reaction products and send them back through line 17 to reactor 10. A slip stream off of the heat treater 16 is removed through line 18 to the heavy ends removal unit 19 (a distillation unit) maintained at temperatures from about 215° C. to about 250° C. The residue from the heavy ends removal unit are sourced from the system through line 20. Most of the volatiles from the heavy ends removal unit 19 are sent back to reactor 10 via line 21.

In the butyl acrylate recovery system, as was stated, the volatile butyl acrylate reaction product is removed from the reactor 10 through line 15 to the finishing distillation tower 24. A small portion of the volatile butyl acrylate reaction product in line 15 is sent through line 23 to the butanol recovery unit 27 maintained at temperatures, from about 95° C. to about 110° C. The volatiles of the butanol recovery unit 27 are sent back via line 28 to the reactor 10 and the residues are removed from the system through line 30. A portion of the highly volatiles of the finishing distillation tower 24, which were separated from the butyl acrylate product recovered through line 26, are recycled to line 15 and the remaining portion sent through line 23 to the butanol recovery unit 27. The residues of the finishing distillation tower 26 are sent back to the reactor 10 through line 29.

In a similar manner as described above, other $C_1$ to $C_8$ alkyl acrylates such as methyl acrylate, ethyl acrylate, propyl acrylate, butyl acrylate, amyl acrylate, hexyl acrylate, heptyl acrylate, octyl acrylate, 2-ethyl hexyl acrylate and the like can be produced. The type of alkyl alcohols which can be used in these reactions include those wherein the alkyl group contains from 1 to 8 carbon atoms such as methyl alcohol, ethyl alcohol, propyl alcohol, butyl alcohol, amyl alcohol, hexyl alcohol, heptyl alcohol, octyl alcohol, 2-ethyl hexyl alcohol and the like.

The acrylic acid added to the reactor 10 can contain inhibitors to prevent undesired polymerization prior to use. Although acrylic acid inhibitors soluble in the reaction mixture can be separately added to the reactor 10, it is preferred that they be added in combination with the acrylic acid and preferable that they be added during the acrylic acid processing. The type of preferred inhibitor present are the phenolic type inhibitors soluble in the acrylic acid such as dihydroxy benzene derivatives such as hydroquinone, catechol, resorcinol, dihydroxybenzene, methoxyphenols such as guaiacol and p-methoxyphenol (methyl ether of hydroquinone) pyrogallol; methylpyrogallol; cresols; phenol; xylenols; 4,4-thiobis - 6 - tertiary - 3 - methylphenol and the like. The amounts of phenol type inhibitors used in this invention are from about 5 parts per million to about 5000 parts per million, preferably from about 25 parts per million to about 500 parts per million based on the total reaction mixture.

Any type of manganese or cerium compound which is soluble in the acrylic acid or reaction mixture can be used in this invention. Suitable manganese compounds include among others, manganous acetate, manganous propionate, manganous nitrate, manganous oxide, manganous hydroxide, manganous chloride, manganous phosphate, manganous perchlorate and the like. Suitable cerium compounds include, among others, ceric ammonium nitrate, cerous ammonium sulfate, cerous benzoate, cerous nitrate, cerous oxalate and the like. The amounts of metal ions used are from about 5 parts per million to about 5000 parts per million, preferably from about 25 to about 500 parts per million of the total reaction mixture.

The esterification catalyst used herein can be any catalyst satisfactory for use in hydrolysis esterification reactions. These include the strong mineral acids such as sulfuric acid, hydrochloric acid, sulfonic acids such as benzenesulfonic acid, toluenesulfonic acid and methanesulfonic acid among others. In this particular invention, the prefered catalyst is methanesulfonic acid. The amounts of esterification catalyst used can range from about 0.1 to about 5 weight percent or higher, preferably from about 1.5 to about 4 weight percent of the total reaction mixture.

The following examples illustrate the process of the invention:

EXAMPLES 1 AND 2

Referring to the description of the drawing in the production of butyl acrylate from butanol and acrylic acid, Example 1 illustrates the results of the reaction without manganese metal ions present compared to the results of Example 2 having manganese metal ions in the reaction. Example 2, representing the process of this invention achieves improvements in acrylic acid efficiency to butyl acrylate over Example 1.

Reactants Fed To Reactor 10

|  | Example 1 | Example 2 |
| --- | --- | --- |
| butyl alcohol pounds/hour | 5087.5 | 3691.7 |
| acrylic acid (assay 97% acrylic acid) pounds per hour | 5033.3 | 3425 |
| Phenothiazine in Reaction mixture (Fed with Acrylic Acid) wt. % of total reaction mixture | 3.0 | 4.0 |
| Manganese metal ions added as manganous acetate fed with acrylic acid parts/million of reaction mixture | 0 | 40-50 |

|  | Example 1 | Example 2 |
| --- | --- | --- |
| Reaction Conditions Reactor 10 |  |  |
| Temperature | 115.6° C. | 115.6° C. |
| Pressure | 180 mm mercury | 180 mm mercury |
| Concentration of base reactants in tower 10 sent through line 14 to Heat Treater 16 | Weight percent of total Reaction mixture | |
| Phenothiazine | 3 | 4.0 |
| Methanesulfonic Acid | 2.5 | 3.8 |
| butyl acrylate range | 8-15 | 8-15 |
| butyl alcohol range | 0.5-1.0 | 0.5-1.0 |
| water range | 0.5-1.0 | 0.5-1.0 |
| base vol. gallons | 10,000 | 10,000 |
| Temperature Heat Treater 16 | 226.7° C. | 226.7° C. |
| Rate of recycle of butyl acrylate, butyl alcohol and water from heat treater 16 through line 17 to reactor 10 | 50 gallons/min | 50 gallons/min |

|  | Example 1 | Example 2 |
| --- | --- | --- |
| Pounds/hour | 8395.8 | 5,820.8 |
| Acrylic acid efficiency to butyl acrylate | 96.7% | 98.6% |
| butanol efficiency to butyl acrylate | 95.4% | 91.2% |

The butanol inefficiency in Example 2(91.2 vs 95.4%) is the result of a higher methanesulfonic acid concentration (required to offset the increase phenothiazine concentration). If the phenothiazine is reduced or eliminated in the system, higher butanol efficiencies will be obtained than the 91.2% of Example 2 containing manganese. These butanol efficiencies will equal or exceed the efficiency of the system without the presence of manganese metal ions.

EXAMPLE 3

In the following example, corrosion rates (expressed in thousands of an inch per year, abbreviated mpy) were determined by use of an electrical resistance - type corrosion probe. The probe is inserted into the process and measurements are taken during operation as the continuing corrosion of the metal reduces the cross-section of the element. A resulting increase in electrical resistance will occur. This result is directly translated, into corrosion rate of the metal.

The following tests were carried out on the reactor (317 stainless steel) product during the production of methyl acrylate from methanol and acrylic acid at a temperature of 140° C. in the presence of 3 weight percent methanesulfonic acid, hydroquinone (400 parts per million), phenothiazine (5000 parts per million) without the presence of manganese metal ions and in another reaction with the presence of manganese metal ions (manganous acetate 100 parts per million). The parts per million are based on the total reaction product.

|  | 317 Stainless Steel Reactor Corrosion Tests | |
| --- | --- | --- |
|  | without manganese metal ions | with manganese metal ions |
| mpy (thousands of an inch per year) | 38.7 (determined on 60 days Operation) | 12.4 (determined on 18 days operation) |

The above results indicate that a 68 percent reduction in corrosion of the stainless steel reactor can be obtained in the use of manganese metal ions with hydroquinone in the production of methyl acrylate from methanol and acrylic acid compared to the reaction without the presence of the manganese metal ions.

What is claimed is:

1. A process for preparing alkyl acrylates wherein the alkyl group contains 1 to 8 carbon atoms comprising reaction an alkyl alcohol containing 1 to 8 carbon atoms with acrylic acid containing a phenolic type inhibitor in the presence of an esterification catalyst selected from the group consisting of strong mineral acids and sulfonic acids, and cerium ions, said ions being soluble in the reaction mixture.

2. The process of claim 1 wherein the cerium ions present are from about 5 parts per million to about 5000 parts per million of the total reaction mixture.

3. The process of claim 2 wherein the cerium ions present are from about 25 parts per million to about 500 parts per million of the total reaction mixture.

4. The process of claim 2 wherein the phenolic type inhibitor is present from about 5 parts per million to about 5,000 parts per million of the total reaction mixture.

5. The process of claim 3 wherein the phenolic type inhibitor is present from about 25 parts per million to about 500 parts per million of the total reaction mixture.

6. The process of claim 5 wherein the phenolic type inhibitor is selected from the group consisting of hydroquinone, p-methoxyphenol, catechol and guaiacol.

7. The process of claim 6 wherein the cerium metal ions are obtained from ceric ammonium nitrate.

8. The process of claim 6 wherein the phenolic type inhibitors is hydroquinone.

9. The process of claim 6 wherein the phenolic type inhibitor is p-methoxyphenol.

10. The process of claim 6 wherein the phenolic type inhibitor is catechol.

11. The process of claim 6 wherein the phenolic type inhibitor is guaiacol.

* * * * *